United States Patent [19]

Meilland

[11] Plant 5,105

[45] Sep. 20, 1983

[54] ROSE PLANT — MEIDOMONAC VARIETY

[75] Inventor: Marie L. Meilland, Antibes, France

[73] Assignee: The Conard-Pyle Company, West Grove, Pa.

[21] Appl. No.: 341,103

[22] Filed: Jan. 20, 1982

[51] Int. Cl.[3] ..... A01H 5/00

[52] U.S. Cl. ..... Plt./1

[58] Field of Search ..... Plt./1, 26

*Primary Examiner*—Robert E. Bagwill

*Attorney, Agent, or Firm*—Burns, Doane, Swecker & Mathis

[57] ABSTRACT

A new and distinct variety of free-branching low growing shrub rose plant is provided having attractive very double flowers which are of a Neyron pink coloration. The new variety resulted from the crossing of an unnamed seedling resulting from the cross of *Rosa sempervirens* and the Mlle. Marthe Carron variety with pollen from the Picasso variety. The new variety is extremely hardy, exceptionally vigorous, and exhibits outstanding disease resistance which renders it well adapted for landscape uses.

17 Drawing Figures

SUMMARY OF THE INVENTION

The object of the present invention is to provide a new variety of rose plant which is distinguished from prior varieties by the following combination of characteristics:

(a) a free-branching low growing shrub growth habit,
(b) abundant formation of very double flowers of Neyron pink coloration,
(c) extreme hardiness,
(d) exceptional vigor, and
(e) good disease resistance.

In view of these characteristics the new variety meets the needs of the horticultural industry for all purposes, and particularly is suited for growing as an attractive ornamental plant in the landscape, e.g. in parks and gardens.

The new variety was created by artificial pollination whereby two parents which previously had been studied for the possible possession of the characteristics sought in the new variety were combined.

The seed parent was an unnamed seedling resulting from the crossing of *Rosa sempervirens* with the Mlle. Marthe Carron variety (non-patented). The pollen parent was the Picasso variety (U.S. Plant Pat. No. 3,351). The parentage of the new variety may be expressed as follows:

[*Rosa sempervirens*×Mlle. Marthe Carron]×Picasso.

The seeds resulting from the above pollination were sown and 191 plantlets were obtained which were physically and biologically different from each other. Selective study resulted in the identification of a single plant of the new variety. The desirable qualities of the new variety have been confirmed through extensive testing and the importance of the new variety has thereby been firmly established.

The new variety has been found to readily undergo propagation by budding and by cuttings. The characteristics of the new variety have been found to be strictly transmissible by such asexual propagation.

The new variety has been named the Meidomonac variety.

BRIEF DESCRIPTION OF THE PHOTOGRAPH

The accompanying photograph shows as nearly true as it is reasonably possible to make the same in a color illustration of this character, typical specimens of plant parts obtained from plants cultivated in greenhouses in Southern France illustrated in:

FIG. 1 — a specimen of a young shoot;

FIG. 2 — a specimen showing a plurality of buds before the opening of the sepals;

FIG. 3 — a specimen of a bud at the opening of the sepals;

FIG. 4 — a specimen showing two buds at the opening of the sepals and in the background two buds before the opening of the sepals;

FIG. 5 — a specimen of a flower while opening as seen from the side;

FIG. 6 — a specimen of a flower while opening as seen from above;

FIG. 7 — a specimen of a fully open flower — plan view — obverse;

FIG. 8 — a specimen of a fully open flower — plan view — reverse;

FIG. 9 — a specimen of a fully open flower immediately prior to petal drop — plan view — obverse;

FIG. 10 — a specimen of a fully open flower immediately prior to petal drop — plan view — reverse;

FIG. 11 — on the left a specimen of a floral receptacle showing the arrangement of the stamens (sepals removed), and on the right a specimen of a floral receptacle showing the arrangement of the pistils (sepals and stamens removed);

FIG. 12 — a specimen showing a plurality of fruits;

FIG. 13 — a specimen showing a portion of a young flowering stem;

FIG. 14 — a specimen showing a portion of a main branch and the appearance of the mature wood;

FIG. 15 — a specimen of a leaf with three leaflets — under surface;

FIG. 16 — a specimen of a leaf with five leaflets — upper surface; and

FIG. 17 — a specimen of a leaf with seven leaflets — upper surface.

DETAILED DESCRIPTION

Figures 1, 2, 3, 4, 7, 8, 9, 12, 15, 16:
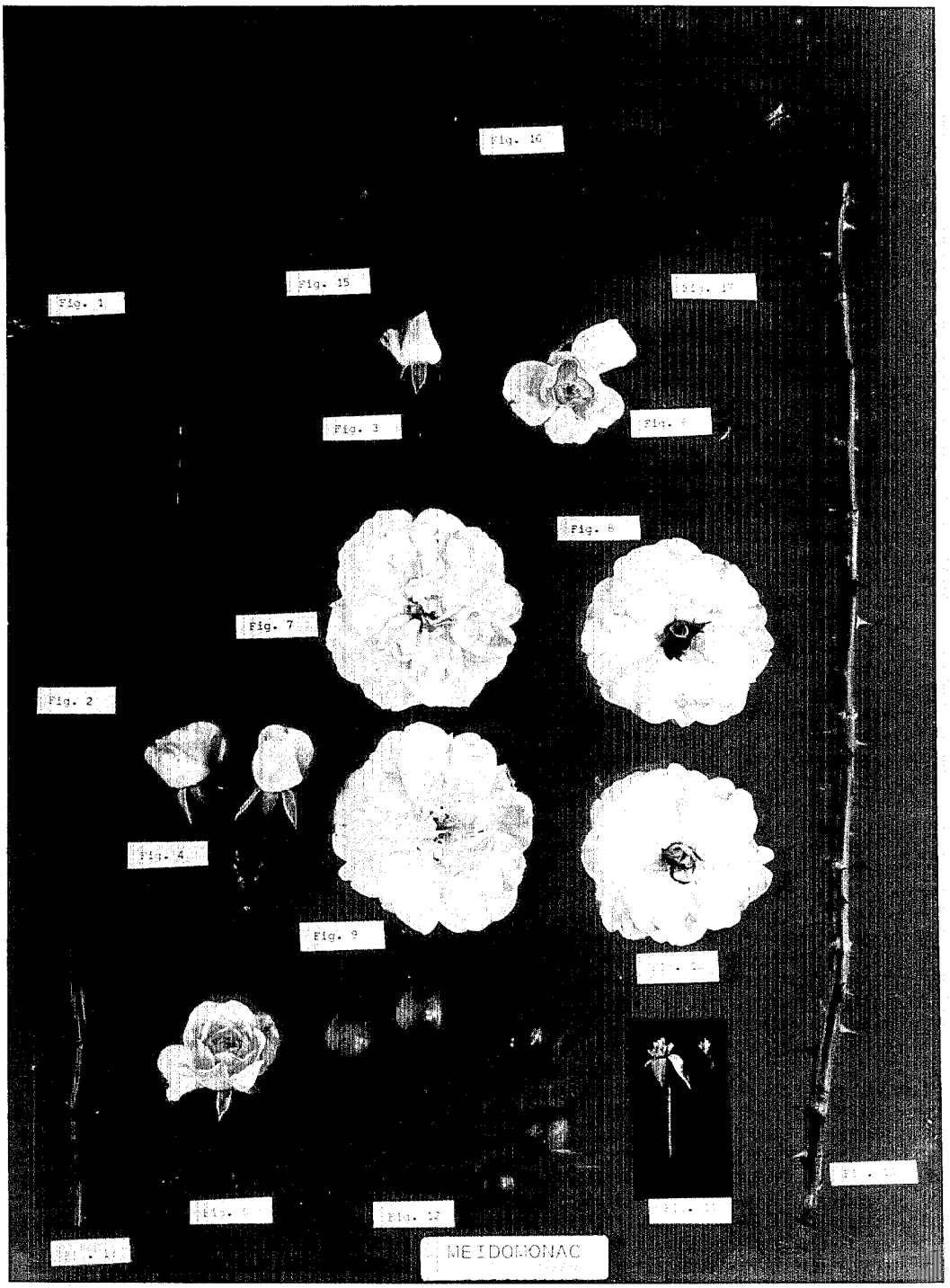

The plants described were grown in greenhouses in Southern France.

The chart used in the identification of the colors is that of The Royal Horticultural Society (R.H.S. Colour Chart). The terminology preceding the numbered references has been added to designate in common terms, the corresponding colors.

Class: Shrub.

Plant:

*Height.*—Approximately 0.8 meter on the average.

*Habit.*—Free-branching and low growing.

Branches:

*Color.*—On young stems: light green 146/B (Yellow-Green Group), sometimes very lightly shaded with reddish coloration. On mature wood: bronze green 146/A (Yellow-Green Group).

*Thorns.*—Shape of upper edge: slightly convex to straight. Shape of under edge: concave. Size: small and lean. Quantity: as illustrated in photograph. Color on young stems: reddish. Color on mature wood: havana brown (common term).

Leaves:

*Stipules.*—Adnate, pectinate, rather wide.

*Petioles.*—Inner surface: grooved, reddish brown on young foliage, medium green on adult foliage, with edges more or less glandular. Outer surface: light green. It very rarely bears small crooked prickles.

*Leaflets.*—Number: 3,5 (most often), and 7. Shape: oval with narrow tip. Serration: simple and regular. Texture: leathery. General appearance: small foliage, dense and semi-dull. Color of young foliage: Upper surface: dark green 147/A (Yellow-Green Group). Under surface: medium green 147/B (Yellow-Green Group) and very slightly shaded with reddish coloration. Color of adult foliage: Upper surface: dark green 147/A (Yellow-Green Group). Under surface: medium green 147/B (Yellow-Green Group).

Inflorescence:

*Number of flowers.*—Multiflorous with up to approximately 20 flowers per stem.

*Peduncle.*—Straight, rigid, often spotted with reddish coloration, very glandular, approximately 2.5 to 3 cm. in length, is free of a crooked prickle.

*Sepals.*—Upper surface: tomentose and light green. Under surface: light green, more or less spotted with reddish coloration, and more or less glandular. The outer sepals may have edges which are more or less appendiculated.

*Buds.*—Shape: ovoid before the opening of the sepals. Length: approximately 1.4 cm. on the average outside the calyx at the opening of the sepals. Size: small. Color when first opening: Interior surface: light Neyron pink 55/D (Red Group). Exterior surface: Neyron pink 55/A (Red Group).

*Flower.*—Form: very double, initially in the shape of a shallow cup and then changing to the shape of a flat cup immediately prior to the petal drop. Diameter: approximately 6 cm. on the average. Color during course of opening: Upper surface: Neyron pink 55/C (Red Group). Under surface: Neyron pink 55/B (Red Group). Color when fully open: Upper surface: Neyron pink 55/C (Red Group). Under surface: Neyron pink 55/B (Red Group). Color immediately prior to petal drop: Upper surface: Neyron pink 56/D (Red Group). Under surface: Neyron pink 55/D (Red Group). Fragrance: nil. Lasting quality: long. Corolla — Petals: texture: consistent. form: rounded with the tip sometimes slightly indented. The unguis is yellowish in coloration with a white border on both surfaces. Number: approximately 53 on average. Stripping: they drop off cleanly. Stamens — Number: approximately 20 on average. They are sometimes not differentiated from the petals. Anthers: orange in coloration. Filaments: greenish in coloration. Pistils — Number: approximately 28 on average. Stigmas: whitish. Styles: free, greenish in coloration, slightly tomentose, some have a fuchsia tip. Receptacle: light green in coloration at the dehiscence of the anthers, and in longitudinal section is very narrow and in the shape of a jug.

Development:

*Vegetation.*—Very vigorous.

*Blossoming.*—Very abundant.

*Aptitude to fruit bearing.*—Very good.

*Hardiness.*—Exceptionally good.

*Resistance to diseases.*—Exceptionally good.

I claim:

1. A new and distinct variety of rose plant, substantially as illustrated and described, characterized by (a) a free-branching low growing shrub growth habit, (b) abundant formation of very double flowers of Neyron pink coloration, (c) extreme hardiness, (d) exceptional vigor, and (e) good disease resistance, whereby the plant is particularly suited for growing as a landscape planting.

* * * * *

ME I DONONAC